United States Patent [19]
Gray et al.

[11] Patent Number: 5,895,406
[45] Date of Patent: Apr. 20, 1999

[54] AXIALLY FLEXIBLE STENT

[75] Inventors: Larry B. Gray, Merrimack, N.H.; Ann Eckert, Easton, Pa.; Todd M Chelak, Lake Hiawatha; Robert M. Tumarkin, Edison, both of N.J.

[73] Assignee: Cordis Corporation, Miami Lakes, Fla.

[21] Appl. No.: 08/770,236

[22] Filed: Dec. 20, 1996

Related U.S. Application Data

[60] Provisional application No. 60/010,686, Jan. 26, 1996, provisional application No. 60/017,479, Apr. 26, 1996, provisional application No. 60/017,415, May 8, 1996, and provisional application No. 60/024,110, Aug. 16, 1996.

[51] Int. Cl.⁶ .......................... A61M 5/00; A61M 29/00
[52] U.S. Cl. .................................. 606/198; 623/1; 623/12
[58] Field of Search ........................ 606/194, 195, 606/198, 200, 1, 108, 191; 128/898; 623/1, 12

[56] References Cited

U.S. PATENT DOCUMENTS

| D. 359,802 | 6/1995 | Fontaine . |
|---|---|---|
| 3,657,744 | 4/1972 | Ersek . |
| 4,441,216 | 4/1984 | Ionescu et al. . |
| 4,503,569 | 3/1985 | Dotter . |
| 4,553,545 | 11/1985 | Maass et al. . |
| 4,580,568 | 4/1986 | Gianturco . |
| 4,733,665 | 3/1988 | Palmaz . |
| 4,776,337 | 10/1988 | Palmaz . |
| 4,800,882 | 1/1989 | Gianturco . |
| 4,856,516 | 8/1989 | Hillstead . |
| 4,886,062 | 12/1989 | Wiltor . |
| 4,907,336 | 3/1990 | Gianturco . |

(List continued on next page.)

FOREIGN PATENT DOCUMENTS

| 0 540 290 A2 | 10/1992 | European Pat. Off. . |
|---|---|---|
| 0 540 290 A3 | 10/1992 | European Pat. Off. . |
| 0734698 A2 | 3/1996 | European Pat. Off. . |
| 0800801 A1 | 8/1996 | European Pat. Off. . |
| 0830853 A1 | 7/1997 | European Pat. Off. . |
| 0 566 807 A1 | 4/1992 | France . |
| 3205942 A1 | 9/1983 | Germany . |
| 1 205 743 | 9/1970 | United Kingdom . |
| 0 662 307 A1 | 12/1994 | United Kingdom . |
| WO96/26689 | 9/1996 | WIPO . |
| WO97/25000 | 7/1997 | WIPO . |

*Primary Examiner*—Michael Buiz
*Assistant Examiner*—William Lewis

[57] ABSTRACT

A stent with axial flexibility, in a preferred embodiment, has a longitudinal axis and comprises a plurality of longitudinally disposed bands, wherein each band defines a generally continuous wave along a line segment parallel to the longitudinal axis. A plurality of links maintains the bands in a tubular structure. In a further embodiment of the invention, each longitudinally disposed band of the stent is connected, at a plurality of periodic locations, by a short circumferential link to an adjacent band.

20 Claims, 7 Drawing Sheets

U.S. PATENT DOCUMENTS

| | | | |
|---|---|---|---|
| 4,969,458 | 11/1990 | Wiktor . | |
| 4,990,131 | 2/1991 | Dardik . | |
| 4,990,155 | 2/1991 | Wilkoff . | |
| 4,994,071 | 2/1991 | MacGregor . | |
| 5,015,253 | 5/1991 | MacGregor . | |
| 5,035,706 | 7/1991 | Gianturco . | |
| 5,041,126 | 8/1991 | Gianturco . | |
| 5,064,435 | 11/1991 | Porter . | |
| 5,102,417 | 4/1992 | Palmaz . | |
| 5,104,404 | 4/1992 | Wolff . | |
| 5,116,365 | 5/1992 | Hillstead . | |
| 5,122,154 | 6/1992 | Rhodes . | |
| 5,131,908 | 7/1992 | Dardik et al. . | |
| 5,133,732 | 7/1992 | Wiktor . | |
| 5,135,536 | 8/1992 | Hillstead . | |
| 5,163,958 | 11/1992 | Pinchuk . | |
| 5,171,262 | 12/1992 | MacGregor . | |
| 5,176,660 | 1/1993 | Truckai . | |
| 5,178,618 | 1/1993 | Kandarpa . | |
| 5,192,307 | 3/1993 | Wall . | |
| 5,195,984 | 3/1993 | Schatz . | |
| 5,217,483 | 6/1993 | Tower . | |
| 5,222,971 | 6/1993 | Willard et al. . | |
| 5,246,445 | 9/1993 | Yachia et al. . | |
| 5,258,021 | 11/1993 | Duran . | |
| 5,266,073 | 11/1993 | Wall . | |
| 5,275,622 | 1/1994 | Lazarus et al. . | |
| 5,282,823 | 2/1994 | Schwartz et al. . | |
| 5,282,824 | 2/1994 | Gianturco . | |
| 5,290,305 | 3/1994 | Inoue . | |
| 5,292,331 | 3/1994 | Boneau | 606/198 |
| 5,304,200 | 4/1994 | Spaulding . | |
| 5,314,444 | 5/1994 | Gianturco . | |
| 5,314,472 | 5/1994 | Fontaine . | |
| 5,334,301 | 8/1994 | Heinke et al. . | |
| 5,342,387 | 8/1994 | Summers . | |
| 5,354,257 | 10/1994 | Roubin et al. . | |
| 5,354,308 | 10/1994 | Simon et al. . | |
| 5,366,504 | 11/1994 | Andersen et al. . | |
| 5,370,683 | 12/1994 | Fontaine . | |
| 5,370,691 | 12/1994 | Samson . | |
| 5,375,612 | 12/1994 | Cottenceau et al. . | |
| 5,376,112 | 12/1994 | Duran . | |
| 5,382,261 | 1/1995 | Palmaz . | |
| 5,387,235 | 2/1995 | Chuter . | |
| 5,389,106 | 2/1995 | Tower . | |
| 5,395,390 | 3/1995 | Simon et al. . | |
| 5,397,355 | 3/1995 | Marin et al. . | |
| 5,403,341 | 4/1995 | Solar . | |
| 5,405,377 | 4/1995 | Cragg . | |
| 5,411,549 | 5/1995 | Peters . | |
| 5,421,955 | 6/1995 | Lau et al. . | |
| 5,423,885 | 6/1995 | Williams . | |
| 5,441,515 | 8/1995 | Khosravi et al. . | |
| 5,441,516 | 8/1995 | Wang et al. . | |
| 5,443,477 | 8/1995 | Marin et al. . | |
| 5,443,496 | 8/1995 | Schwartz et al. . | |
| 5,443,498 | 8/1995 | Fontaine . | |
| 5,443,500 | 8/1995 | Sigwart . | |
| 5,449,372 | 9/1995 | Schmaltz et al. . | |
| 5,449,373 | 9/1995 | Pinchasik et al. | 606/198 |
| 5,449,382 | 9/1995 | Dayton . | |
| 5,496,365 | 3/1996 | Fontaine et al. . | |
| 5,527,354 | 6/1996 | Fontaine et al. . | |
| 5,540,712 | 7/1996 | Kleshinski et al. | 606/198 |
| 5,569,295 | 10/1996 | Lam . | |
| 5,591,197 | 1/1997 | Orth et al. . | |
| 5,607,442 | 3/1997 | Fischell et al. | 606/198 |
| 5,643,312 | 7/1997 | Fischell et al. . | |
| 5,649,952 | 7/1997 | Lam . | |
| 5,653,747 | 8/1997 | Dereume | 623/1 |
| 5,695,516 | 12/1997 | Fischell et al. | 606/198 |
| 5,697,971 | 12/1997 | Fischell et al. . | |

AXIALLY FLEXIBLE STENT

CROSS REFERENCE

This application claims the benefit of the earlier filing dates of U.S. provisional applications: 60/010,686 filed Jan. 26, 1996; 60/017,479 filed Apr. 26, 1996; 60/017,415 filed May 8, 1996; 60/024,110, filed Aug. 16, 1996 incorporated herein by reference.

TECHNICAL FIELD

The present invention relates to a stent having axial flexibility and resilience in its expanded form.

BACKGROUND ART

A stent is commonly used as a tubular structure left inside the lumen of a duct to relieve an obstruction. Commonly, stents are inserted into the lumen in a non expanded form and are then expanded autonomously (Tihon et al. (1994) U.S. Pat. No. 5,356,423) or with the aid of a second device in situ. Although a number of designs have been reported, these designs have suffered from a number of limitations. These include; restrictions on the dimension of the stent (Cardon et al. 1995 U.S. Pat. No 5,383,892). Cardon et al. describes a stent that has rigid ends (8 mm) and a flexible median part of 7–21 mm. This device is formed of multiple parts and is not continuously flexible along the longitudinal axis. Another stent design that has rigid segments and flexible segments has been described by Pinchasik et al. U.S. Pat. No. 5,449,373 (1995).

Other stents are described as longitudinally flexible (Lau et al.(1995) U.S. Pat. No. 5,421,955 also EP application 540290 A2, A3) but consist of a plurality of cylindrical elements connected by flexible members. This design has at least one important disadvantage, for example, according to this design, protruding edges occur when the stent is flexed around a curve raising the possibility of inadvertent retention of the stent on plaque deposited on arterial walls. This may cause the stent to embolize or move out of position and further cause damage to the interior lining of healthy vessels. (see FIG. 1(a) below).

Thus, stents known in the art, which may be expanded by balloon angioplasty, generally compromise axial flexibility to permit expansion and provide overall structural integrity.

SUMMARY OF THE INVENTION

The present invention overcomes some perceived shortcomings of prior art stents by providing a stent with axial flexibility. In a preferred embodiment, the stent has a first end and a second end with an intermediate section between the two ends. The stent further has a longitudinal axis and comprises a plurality of longitudinally disposed bands, wherein each band defines a generally continuous wave along a line segment parallel to the longitudinal axis. A plurality of links maintains the bands in a tubular structure. In a further embodiment of the invention, each longitudinally disposed band of the stent is connected, at a plurality of periodic locations, by a short circumferential link to an adjacent band. The wave associated with each of the bands has approximately the same fundamental spatial frequency in the intermediate section, and the bands are so disposed that the waves associated with them are spatially aligned so as to be generally in phase with one another. The spatially aligned bands are connected, at a plurality of periodic locations, by a short circumferential link to an adjacent band.

In particular, at each one of a first group of common axial positions, there is a circumferential link between each of a first set of adjacent pairs of bands.

At each one of a second group of common axial positions, there is a circumferential link between each of a second set of adjacent rows of bands, wherein, along the longitudinal axis, a common axial position occurs alternately in the first group and in the second group, and the first and second sets are selected so that a given band is linked to a neighboring band at only one of the first and second groups of common axial positions.

In a preferred embodiment of the invention, the spatial frequency of the wave associated with each of the bands is decreased in a first end region lying proximate to the first end and in a second end region lying proximate to the second end, in comparison to the spatial frequency of the wave in the intermediate section. In a further embodiment of the invention, the spatial frequency of the bands in the first and second end regions is decreased by 20% compared with the spatial frequency of the bands in the intermediate section. The first end region may be located between the first end and a set of circumferential links lying closest to the first end and the second end region lies between the second end and a set of circumferential links lying closest to the second end. The widths of corresponding sections of the bands in these end regions, measured in a circumferential direction, are greater in the first and second end regions than in the intermediate section. Each band includes a terminus at each of the first and second ends and the adjacent pairs of bands are joined at their termini to form a closed loop.

In a further embodiment of the invention, a stent is provided that has first and second ends with an intermediate section therebetween, the stent further having a longitudinal axis and providing axial flexibility. This stent includes a plurality of longitudinally disposed bands, wherein each band defines a generally continuous wave having a spatial frequency along a line segment parallel to the longitudinal axis, the spatial frequency of the wave associated with each of the bands being decreased in a first end region lying proximate to the first end and in a second end region lying proximate to the second end, in comparison to the spatial frequency of the wave in the intermediate section; and a plurality of links for maintaining the bands in a tubular structure. The first and second regions have been further defined as the region that lies between the first and second ends and a set of circumferential links lying closest lying closest to the first end and second end.

In a further embodiment the widths of the sections of the bands, measured in a circumferential direction, are greater in the first and second end regions than in the intermediate section.

BRIEF DESCRIPTION OF THE DRAWINGS

The foregoing aspects of the invention will be more readily understood by reference to the following detailed description, taken with the accompanying drawings, in which.

DETAILED DESCRIPTION OF SPECIFIC EMBODIMENTS

Improvements afforded by embodiments of the present invention include (a) increased flexibility in two planes of the non-expanded stent while maintaining radial strength and a high percentage open area after expansion; (b) even pressure on the expanding stent that ensures the consistent and continuous contact of expanded stent against artery wall; (c) avoidance of protruding parts during bending; (d) removal of existing restrictions on maximum length of stent; and reduction of any shortening effect during expansion of the stent.

Figure 7:
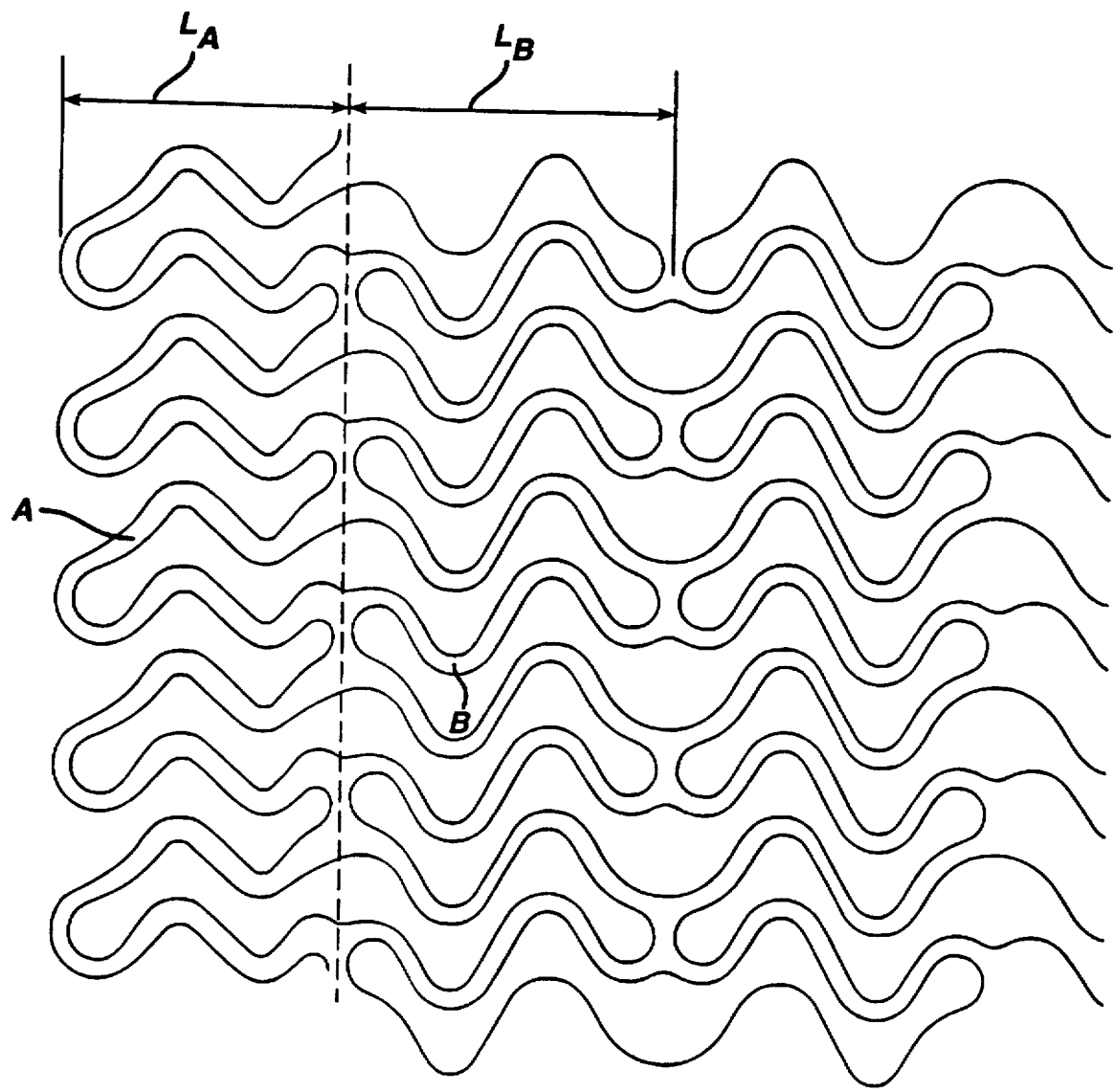
FIG. 7 shows a two dimensional layout of the stent. The ends are modified such that the length ($L_A$) is about 20% shorter than length ($L_B$) and the width of the band A is greater than the width of band B.

In a preferred embodiment of the invention, an expandable cylindrical stent is provided having a fenestrated structure for placement in a blood vessel, duct or lumen to hold the vessel, duct or lumen open, more particularly for protecting a segment of artery from restenosis after angioplasty. The stent may be expanded circumferentially and maintained in an expanded configuration, that is circumferentially rigid. The stent is axially flexible and when flexed at a band, the stent avoids any externally protruding component parts. FIG. 1 shows what happens to a stent, of a similar design to a preferred embodiment herein but utilizing instead a series of circumferentially disposed bands, when caused to bend in a manner that is likely encountered within a lumen of the body. A stent with a circumferential arrangement of bands (1) experiences an effect analogous to a series of box cars on a railway track. As the row of box cars proceeds around the bend, the corner of each car proceeding around the bend after the coupling is caused to protrude from the contour of the track. Similarly, the serpentine circumferential bands have protrusions (2) above the surface of the stent as the stent bends. In contrast, the novel design of the embodiment shown in FIGS. 1(c) and 1(d) and FIG. 7 in which the bands (3) are axially flexible and are arranged along the longitudinal axis, avoids the box car effect when the stent is bent, so the bent bands (4) do not protrude from the profile of the curve of the stent. Furthermore, any flaring at the ends of the stent that might occur with a stent having a uniform structure is substantially eliminated by introducing a modification at the ends of the stent. This modification comprises decreasing the spatial frequency and increasing the width of the corresponding bands in a circumferential direction ($L_A$ and A) compared to that of the intermediate section. ($L_B$ and B). Other modifications at the ends of the stent may include increasing the thickness of the wall of the stent and selective electropolishing. These modifications protect the artery and any plaque from abrasion that may be caused by the stent ends during insertion of the stent. The modification also may provide increased radio-opacity at the ends of the stent. Hence it may be possible to more accurately locate the stent once it is in place in the body.

Figure 1A:
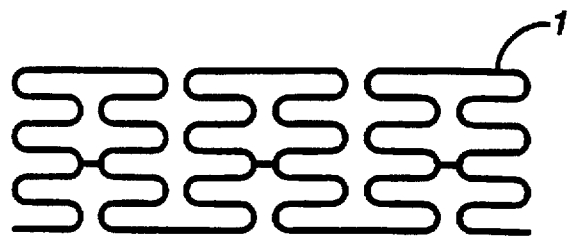
FIGS. 1(a) and 1(b) are side views of a stent having circumferentially disposed bands wherein the stent is in axially unbent and bent positions respectively, the latter showing protruding edges.
Figure 1B:
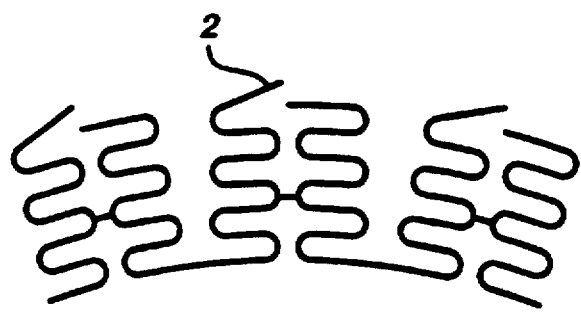
Figure 1C:
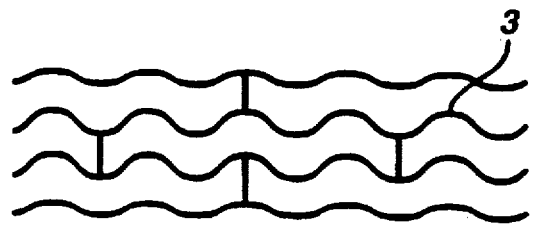
FIGS. 1(c) and 1(d) are side views of an axially flexible stent in accordance with the present invention wherein the stent is in unbent and bent positions respectively, the latter displaying an absence of protruding edges.
Figure 1D:
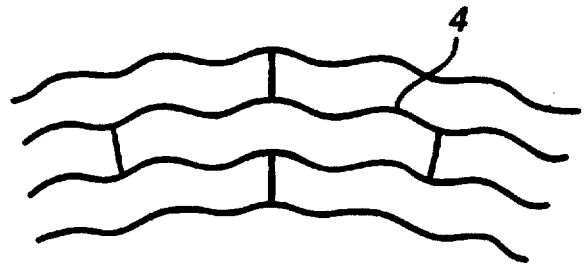
Figure 2:
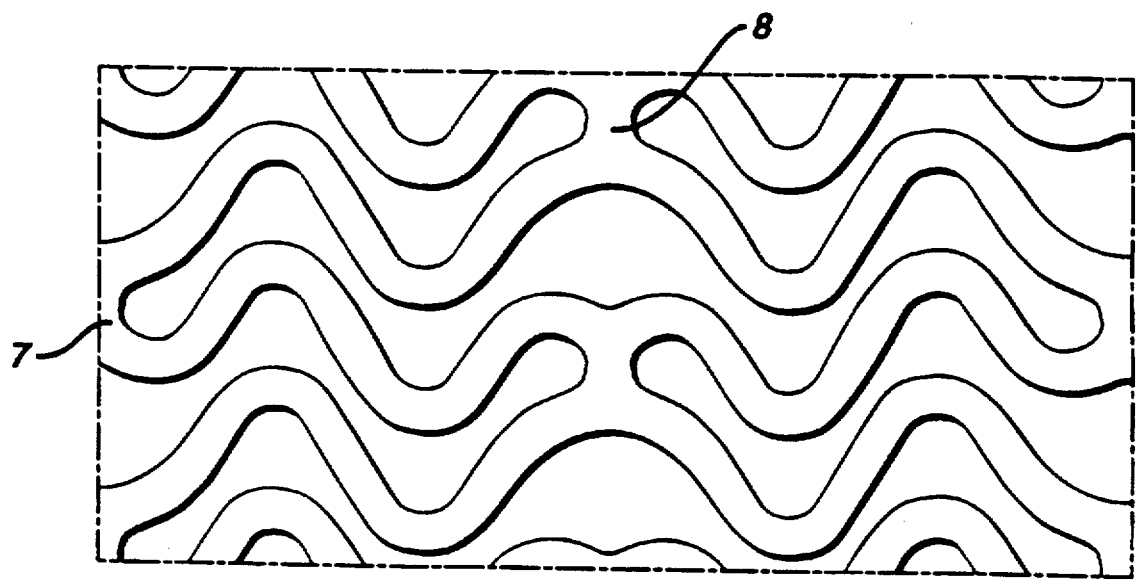
FIG. 2 is a side view of a portion of the stent of FIGS. 1(c) and 1(d) showing the longitudinal bands, spaces, and inner radial measurements of bends in the bands being measured in inches.
Figure 6:
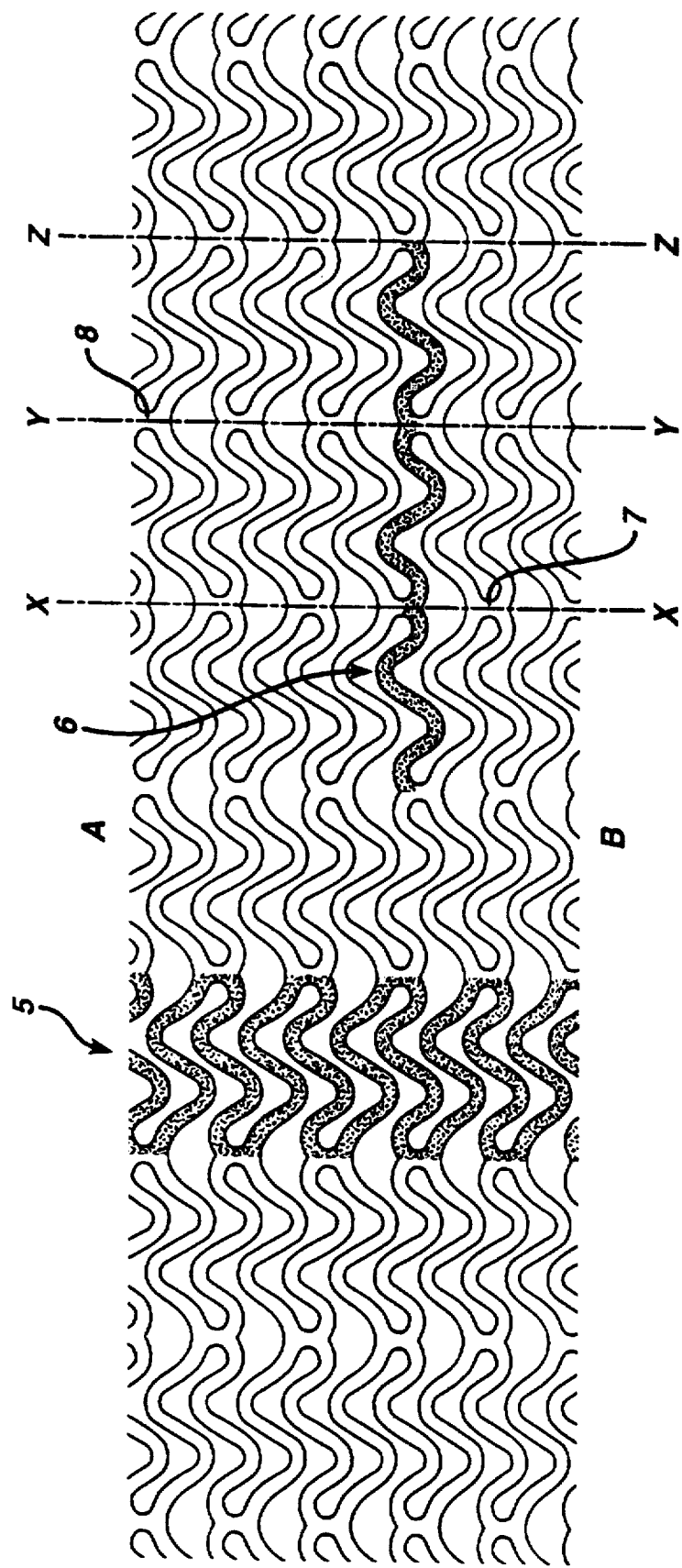
FIG. 6 shows a two-dimensional layout of the stent of FIG. 4 to form a cylinder such that edge "A" meets edge "B", and illustrating the spring-like action provided in circumferential and longitudinal directions.

The embodiment as shown in FIGS. 2 and 6 has the unique advantage of possessing effective "springs" in both circumferential and longitudinal directions shown as items (5) and (6) respectively. These springs provide the stent with the flexibility necessary both to navigate vessels in the body with reduced friction and to expand at the selected site in a manner that provides the final necessary expanded dimensions without undue force while retaining structural resilience of the expanded structure.

Figure 4:
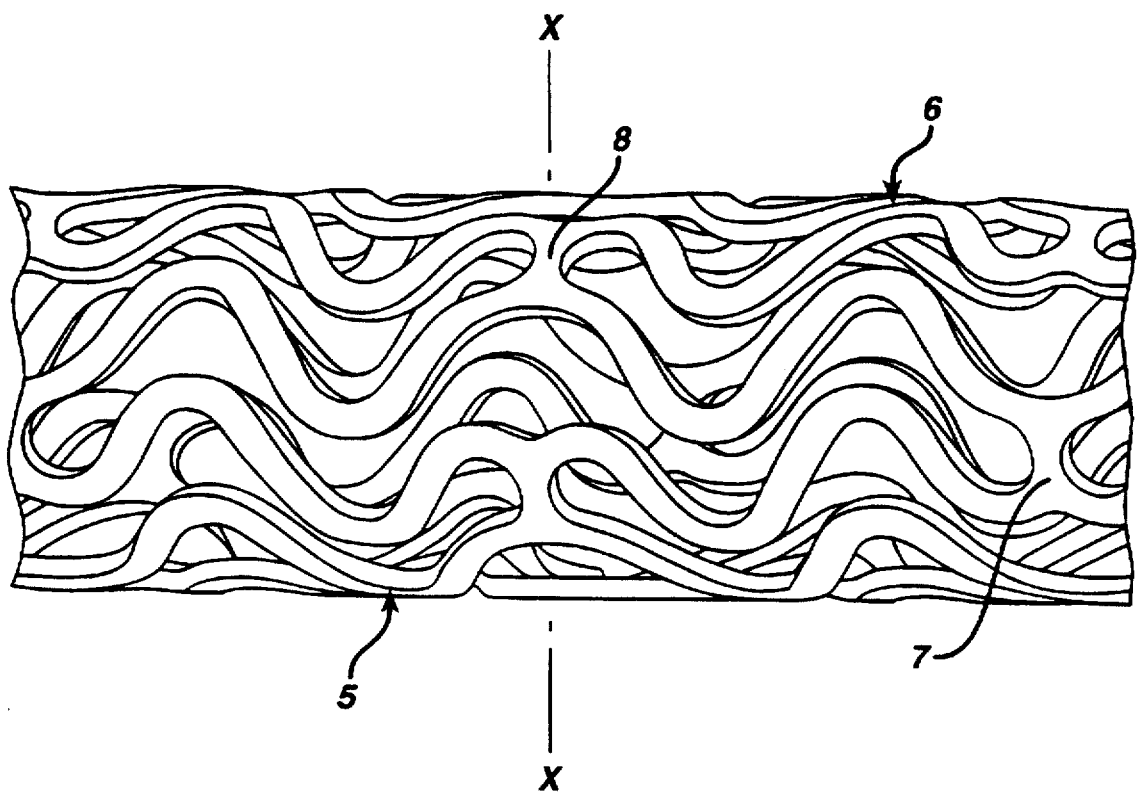
FIG. 4 is a view along the length of a piece of cylindrical stent (ends not shown) prior to expansion showing the exterior surface of the cylinder of the stent and the characteristic banding pattern.
Figure 5:
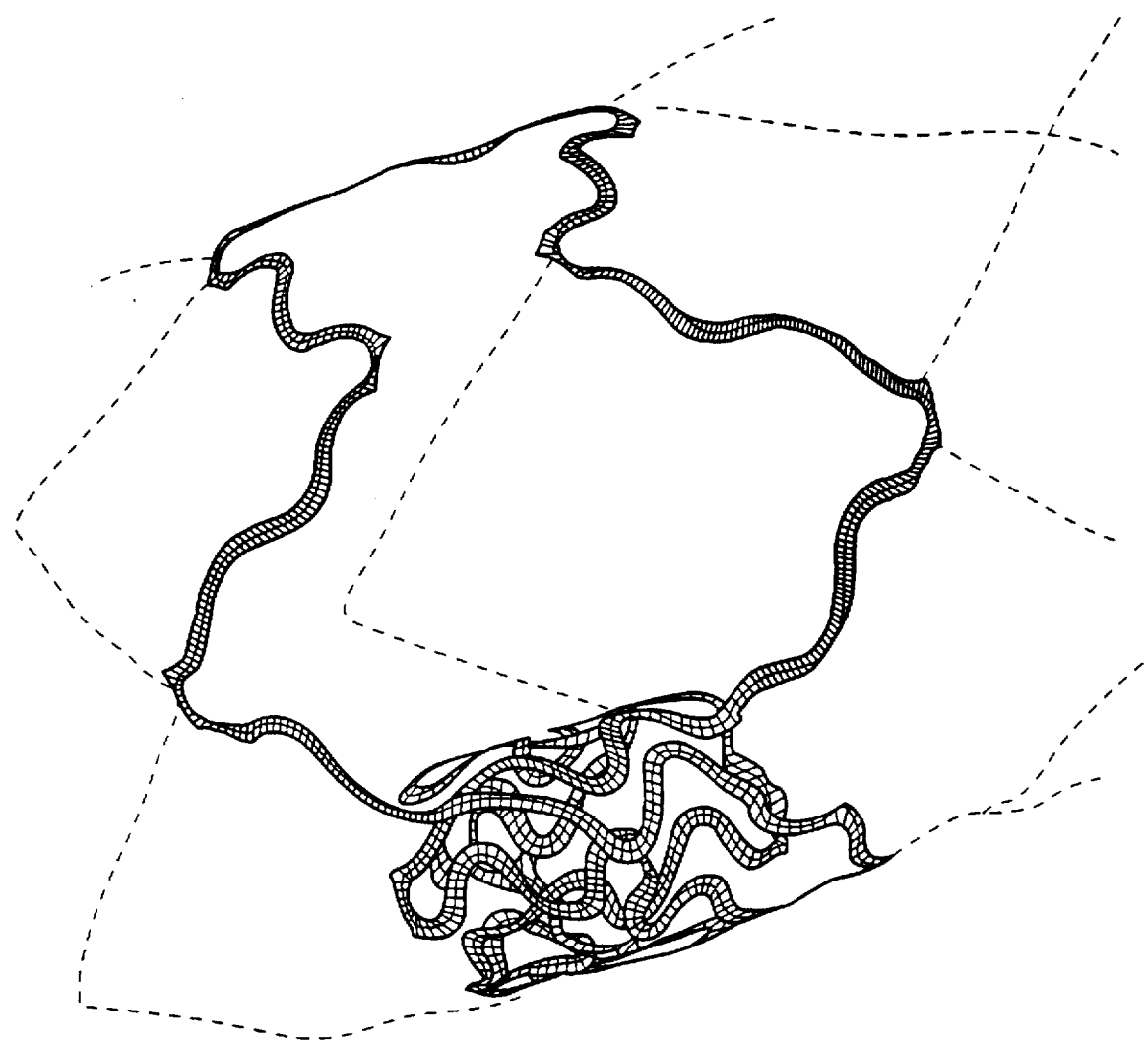
FIG. 5 is an isometric view of a deflection plot where the stent of FIG. 2 is expanded to a larger diameter of 5 mm.

As shown in both FIGS. 2, 4 and 6, each longitudinal band undulates through approximately two cycles before there is formed a circumferential link to an adjacent band. Prior to expansion, the wave associated with each of the bands may have approximately the same fundamental spatial frequency, and the bands are so disposed that the waves associated with them are spatially aligned, so as to be generally in phase with one another as shown in FIG. 6.

The aligned bands on the longitudinal axis are connected at a plurality of periodic locations, by a short circumferential link to an adjacent band. Consider a first common axial position such as shown by the line X—X in FIG. 4 and 6. Here an adjacent pair of bands is joined by circumferential link 7. Similarly other pairs of bands are also linked at this common axial position. At a second common axial position, shown in FIG. 6 by the line Y—Y, an adjacent pair of bands is joined by circumferential link 8. However, any given pair of bands that is linked at X—X is not linked at Y—Y and vice-versa. The X—X pattern of linkages repeats at the common axial position Z—Z. In general, there are thus two groups of common axial positions. In each of the axial positions of any one group are links between the same pairs of adjacent bands, and the groups alternate along the longitudinal axis of the embodiment. In this way, circumferential spring 5 and the longitudinal spring 6 are provided.

A feature of the expansion event is that the pattern of open space in the stent of the embodiment of FIG. 2 before expansion is different from the pattern of the stent after expansion. In particular, in a preferred embodiment, the pattern of open space on the stent before expansion is serpentine, whereas after expansion, the pattern approaches a diamond shape (3a, 3b). In embodiments of the invention, expansion may be achieved using pressure from an expanding balloon or by other mechanical means.

Figure 3A:
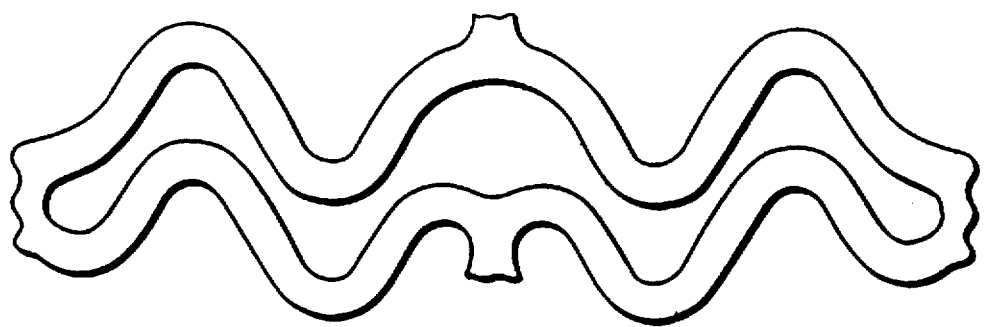
FIGS. 3 (a) and 3 (b) show a portion of the stent of FIG. 2 with two bands between two circumferential links (a) before expansion in the undeformed state; and (b) after expansion, in the deformed state.
Figure 3B:
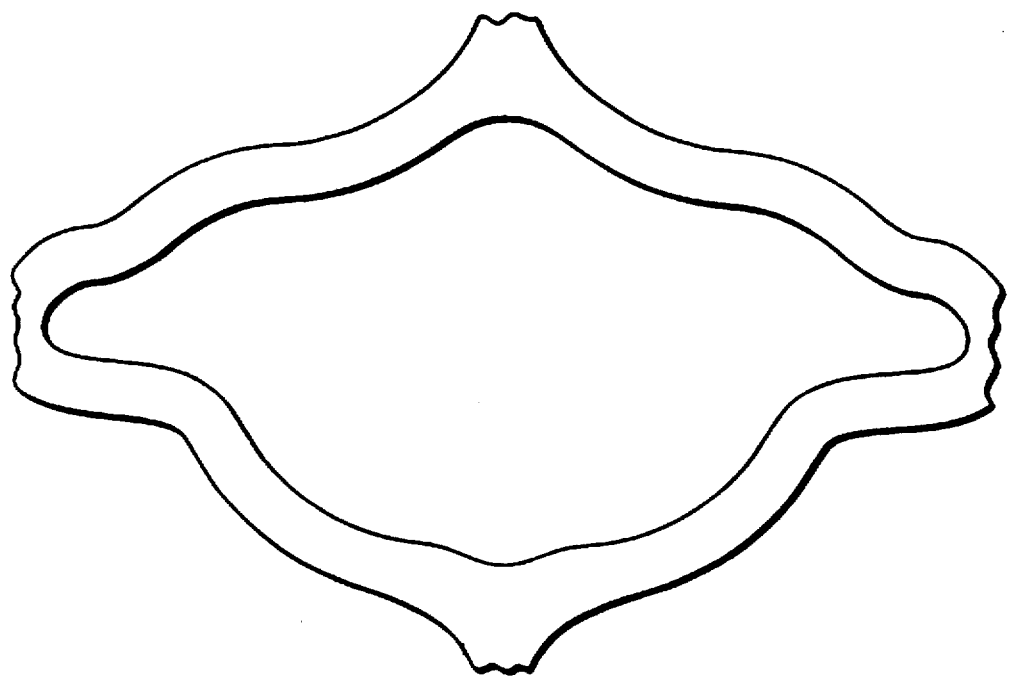

In the course of expansion, as shown in FIG. 3, the wave shaped bands tend to become straighter. When the bands become straighter, they become stiffer and thereby withstand relatively high radial forces. FIG. 3 shows how radial expansion of the stent causes the fenestra to open up into a diamond shape with maximum stress being expended on the apices of the diamond along the longitudinal axis. When finite element analyses including strain studies were performed on the stent, it was found that maximum strain was experienced on the bands and links and was below the maximum identified as necessary to maintain structural integrity.

The optimization of strain and "pop" pressure of the stent is achieved by creating as large a turn radius as possible in the wave associated with each band in the non-expanded stent while preserving a sufficient number of bands and links to preserve the structural integrity of the stent after expansion. The number of bands and the spatial frequency of the wave they describe on the longitudinal axis also affects the number of circumferential links. The circumferential links contribute structural integrity during application of radial force used in expansion of the stent and in the maintenance of the expanded form.

The stent may be fabricated from many methods. For example, the stent may be fabricated from a hollow or formed stainless steel tube that may be cut out using lasers, electric discharge milling (EDM), chemical etching or other means. The stent is inserted into the body and placed at the desired site in an unexpanded form. In a preferred embodiment, expansion of the stent is effected in a blood vessel by means of a balloon catheter, where the final diameter of the stent is a function of the diameter of the balloon catheter used.

In contrast to stents of the prior art, the stent of the invention can be made at any desired length, most preferably at a nominal 30 mm length that can be extended or diminished by increments, for example 1.9 mm increments.

It will be appreciated that a stent in accordance with the present invention may be embodied in a shape memory material, including, for example, an appropriate alloy of nickel and titanium; or stainless steel. In this embodiment after the stent has been formed, it may be compressed so as to occupy a space sufficiently small as to permit its insertion in a blood vessel or other tissue by insertion means, wherein the insertion means include a suitable catheter, or flexible rod. On emerging from the catheter, the stent may be configured to expand into the desired configuration where the expansion is automatic or triggered by a change in pressure, temperature or electrical stimulation.

An embodiment of the improved stent has utility not only within blood vessels as described above but also in any tubular system of the body such as the bile ducts, the urinary system, the digestive tube, and the tubes of the reproductive system in both men and women.

What is claimed is:

1. A stent having first and second ends with an intermediate section therebetween, and a longitudinal axis, comprising:

a plurality of longitudinally disposed bands, wherein each band defines a generally continuous wave having a spatial frequency along a line segment parallel to the longitudinal axis; and a plurality of links for maintaining the bands in a tubular structure, wherein the links are so disposed that any single circumferential path formed by the links is discontinuous;

such that the links and bands define an expandable structure having axial flexibility in an unexpanded configuration.

2. A stent according to claim 1, wherein each link is axially displaced from any circumferentially adjacent link.

3. A stent according to claim 2, wherein the spatial frequency of the wave associated with each of the bands, is decreased in a first end region lying proximate to the first end and in a second end region lying proximate to the second end, in comparison to the spatial frequency of the wave in the intermediate section.

4. A stent according to claim 3, wherein the spatial frequency is decreased by about 20% compared with the spatial frequency of the wave in the intermediate section.

5. A stent according to claim 4, wherein the first end region lies between the first end and a set of circumferential links lying closest to the first end and the second end region lies between the second end and a set of circumferential links lying closest to the second end.

6. A stent according to claim 5, wherein widths of corresponding sections of the bands, measured in a circumferential direction, are greater in the first and second end.

7. A stent according to claim 3, wherein the first end region lies between the first end and a set of circumferential links lying closest to the first end and the second end region lies between the second end and a set of circumferential links lying closest to the second end.

8. A stent according to claim 7, wherein widths of corresponding sections of the bands, measured in a circumferential direction, are greater in the first and second end regions than in the intermediate section.

9. A stent according to claim 3, wherein widths of corresponding sections of the bands, measured in a circumferential direction, are greater in the first and second end regions than in the intermediate section.

10. A stent according to claim 3, wherein each band includes a terminus at each of the first and second ends and the adjacent pairs of bands are joined at their termini to form a closed loop.

11. A stent according to claim 1, wherein the wave associated with each of the bands has approximately the same fundamental spatial frequency for the intermediate section.

12. A stent according to claim 11, wherein the bands are so disposed that the waves associated with them are spatially aligned so as to be generally in phase with one another.

13. A stent according to claim 12, wherein each link is axially displaced from any circumferentially adjacent link.

14. A stent according to claim 13, wherein, at each one of a first group of common axial positions, there is a circumferential link between each of a first set of adjacent pairs of bands.

15. A stent according to claim 13, wherein, at each one of a second group of common axial positions, there is a circumferential link between each of a second set of adjacent rows of bands, wherein, along the longitudinal axis, a common axial position occurs alternately in the first group and in the second group, and the first and second sets are selected so that a given band is linked to a neighboring band at only one of the first and second groups of common axial positions.

16. A stent according to claim 15, wherein the spatial frequency of the wave associated with each of the bands, is decreased in a first end region lying proximate to the first end and a second end region lying proximate to the second end, in comparison to the spatial frequency of the wave in the intermediate section.

17. A stent according to claim 1, wherein each band includes a terminus at each of the first and second ends and the adjacent pairs of bands are joined at their termini to form a closed loop.

18. A stent having first and second ends with an intermediate section therebetween, the stent further having a longitudinal axis, comprising:

(a) a plurality of longitudinally disposed bands, wherein each band defines a generally continuous wave having a spatial frequency along a line segment parallel to the longitudinal axis; the spatial frequency of the wave associated with each of the bands being decreased in a first end region lying proximate to the first end and in a second end region lying proximate to the second end, in comparison to the spatial frequency of the wave in the intermediate section; and (b) a plurality of links for maintaining the bands in a tubular structure; such that the links and bands define an expandable structure having axial flexibility in an unexpanded configuration.

19. A stent according to claim 18, wherein widths of sections of the bands, measured in a circumferential direction, are greater in the first and second end regions than in the intermediate section.

20. A stent having first and second ends with an intermediate section therebetween, and a longitudinal axis, comprising:

a plurality of longitudinally disposed bands; and a plurality of links for maintaining the bands in a tubular structure, wherein each band is connected at a plurality of periodic locations by a circumferential link to an adjacent band, each link being axially displaced from any circumferentially adjacent link; such that the links and bands define an expandable structure having axial flexibility in an unexpanded configuration.

* * * * *